United States Patent [19]
Deuar

[11] Patent Number: 5,212,654
[45] Date of Patent: May 18, 1993

[54] TESTING OF POLES

[76] Inventor: Krzysztof J. Deuar, 17 Henderson Road, Burpengary, Queensland, 4505, Australia

[21] Appl. No.: 763,466

[22] Filed: Sep. 23, 1991

Related U.S. Application Data

[63] Continuation-in-part of Ser. No. 546,744, Jul. 2, 1990, Pat. No. 5,051,919, which is a continuation-in-part of Ser. No. 396,089, Aug. 21, 1989, abandoned, which is a continuation of Ser. No. 272,477, Nov. 17, 1988, abandoned, which is a continuation of Ser. No. 96,482, Sep. 15, 1987, abandoned.

[30] Foreign Application Priority Data

Apr. 22, 1987 [AU] Australia ............................ 71869/87
Jul. 31, 1989 [AU] Australia ............................ 39091/89
Aug. 1, 1991 [AU] Australia ............................ 81530/91

[51] Int. Cl.$^5$ .............................................. G01N 3/20
[52] U.S. Cl. ...................................... 364/508; 73/786; 73/849
[58] Field of Search ............... 364/508, 507, 506, 505, 364/512; 73/849, 816, 807, 788, 786; 254/30, 29 R

[56] References Cited

U.S. PATENT DOCUMENTS

| 2,283,730 | 5/1942 | Gardner. |
| 2,854,847 | 10/1958 | Brady .................................. 73/786 |
| 3,733,049 | 5/1973 | van den Hove et al. ........... 364/508 |
| 4,366,874 | 1/1983 | Pidoux et al. .................... 364/508 X |
| 4,464,937 | 8/1984 | Watts et al. ...................... 73/788 X |
| 4,574,356 | 3/1986 | Schattschneider et al. ........ 364/508 |
| 4,582,013 | 4/1986 | Holland, Jr. ....................... 114/102 |
| 5,051,919 | 9/1991 | Deuar ................................ 364/508 |

Primary Examiner—Thomas G. Black
Assistant Examiner—Ellis B. Ramirez
Attorney, Agent, or Firm—Foley & Lardner

[57] ABSTRACT

The residual strength of electricity poles is determined by the deflection of the poles under a pre-determined applied load. The load is applied by an extensible ram which has a foot secured to the base of the pole by a chain and a head plate with teeth which engages the sides of the poles. A preset hydraulic pressure is applied to the ram by a manual pump and the deflection if measured by strain gauges mounted on a support frame. The load deflection data are fed to a programmed computer which calculates the residual strength.

23 Claims, 11 Drawing Sheets

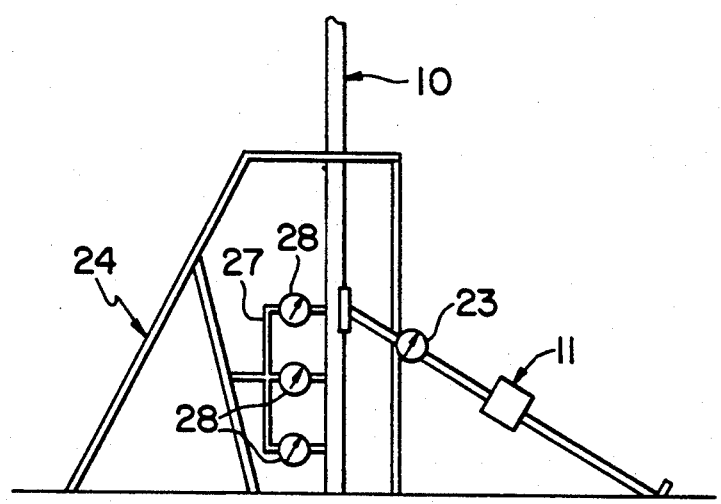
FIG.1
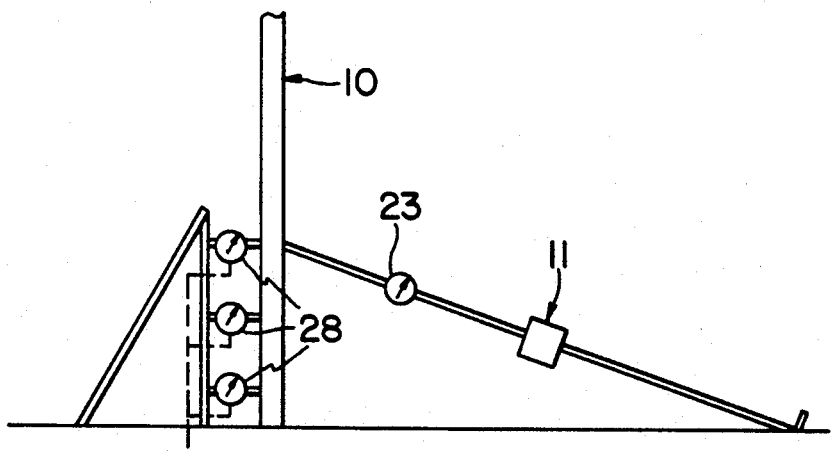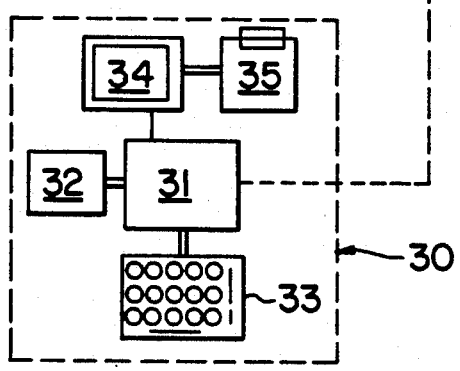
FIG.2

TESTING OF POLES

This application is a continuation-in-part application of Ser. No. 07/546,744, filed Jul. 2, 1990, now U.S. Pat. No. 5,051,919, which is in turn, a continuation-in-part application of Ser. No. 07/396,089, filed Aug. 21, 1989, abandoned, which is in turn a continuation application of Ser. No. 07/272,477, filed Nov. 17, 1988, now abandoned, which is in turn a continuation application of Ser. No. 07/096,482, filed Sep. 15, 1987, now abandoned.

BACKGROUND OF THE INVENTION

1. Field of the Invention

This invention relates to a method of, and apparatus for, the testing of poles. (Throughout the specification, the term "poles" shall be used to include electricity, telephone and telegraph poles; fence and retaining wall posts and the like.

The term "residual strength" is a measurement of the load which can be applied to a pole before the pole will fail, and is less than the original strength of the pole due to decay, cracking and other factors.

2. Prior Art

Wood rot, bores, termites and other factors operate to reduce the strength, and therefore, the service life of poles. For safety reasons, the strength of the poles must be periodically checked and the future life of the pole established. As wood rot generally occurs below ground level, a simple visual inspection is not sufficient and mechanical strength tests must be carried out.

To date, no simple, efficient and reliable test method has been available so poles are often replaced well before the end of their effective life. This naturally increases the operating expenses of the electricity authority.

SUMMARY OF THE PRESENT INVENTION

It is an object to provide at least one simple method for testing the poles.

It is a preferred object to provide an apparatus suitable for the method.

It is a further preferred object to provide a method where the remaining life of the poles can be calculated.

Other preferred objects will become apparent from the following description.

In one aspect, the present invention resides in a method for the non-destructive testing of the residual strength of a pole including the steps of:
applying a preset load to the pole above ground level;
measuring the displacement of the pole under the load; and
from the applied load and the displacement, calculating the residual strength of the pole from predetermined formula(e), or by a programmed calculator or computer.

In a second aspect, the present invention relates to a method for the non-destructive testing of the residual strength of a pole including the steps of:
applying a load to the pole above ground level to cause the pole to undergo a preset displacement;
measuring the load applied to the pole; and
from the applied load and the displacement, calculating the residual strength of the pole from predetermined formula(e), or by a programmed calculator or computer.

In a third aspect, the present invention resides in a method for the non-destructive testing of the residual strength of a pole including the steps of:
calculating the minimum required strength of the pole including any required safety factors;
applying a preset load to the pole above ground level equivalent to the calculated minimum strength; and
observing if the pole withstands the applied load without failure and so meet the minimum required strength.

In a fourth aspect, the present invention resides in an apparatus for the non-destructive measurement of the residual strength of a pole according to any of the methods hereinbefore described, the apparatus including:
means to apply a load to the pole above ground level;
load cell means to measure the load applied to the pole;
means to measure the displacement of the pole under the applied load; and
means to calculate the residual strength of the pole from the applied load and the displacement.

The load may be applied by either pushing or pulling the pole at a height of, eg. 1–2 m above ground level and may be effected by a mechanical jack or turnbuckle, a hydraulic or pneumatic ram, a winch or other suitable mechanical, hydraulic or electrical means.

The applied load is preferably measured by a load cell or other suitable equivalent means.

The displacement of the pole in both deflection and rotation about its vertical arm as well as deformation of the pole is preferably measured and this may be effected by displacement gauges mounted on, or around, a reference frame, strain gauges or the like.

The applied loads, displacements and deformations of the pole may be recorded manually or automatically by the use of any suitable computer system.

Stability of the pole in case of its failure can be provided by a safety frame, safety rope or safety clamps mounted to the boom of the crane, of the pole testing vehicle or other heavy equipment.

The excessive movement of the pole at ground level is limited by a chain, rope, frame, bar or clamps connected to the pole testing equipment or other heavy and stable machinery and objects such as concrete blocks, adjacent trees or the like.

The residual strength and other test parameters may be calculated from predetermined formula(e) or be fed into a programmed calculation or computer.

BRIEF DESCRIPTION OF THE DRAWINGS

To enable the invention to be fully understood, preferred embodiments will now be described with reference to the accompanying drawings, in which:

FIG. 1 is a schematic view showing a pole being tested under a preset applied load;

FIG. 2 is a similar view showing a pole being tested under a preset displacement;

DETAILED DESCRIPTION OF THE PREFERRED EMBODIMENTS

Figure 3:
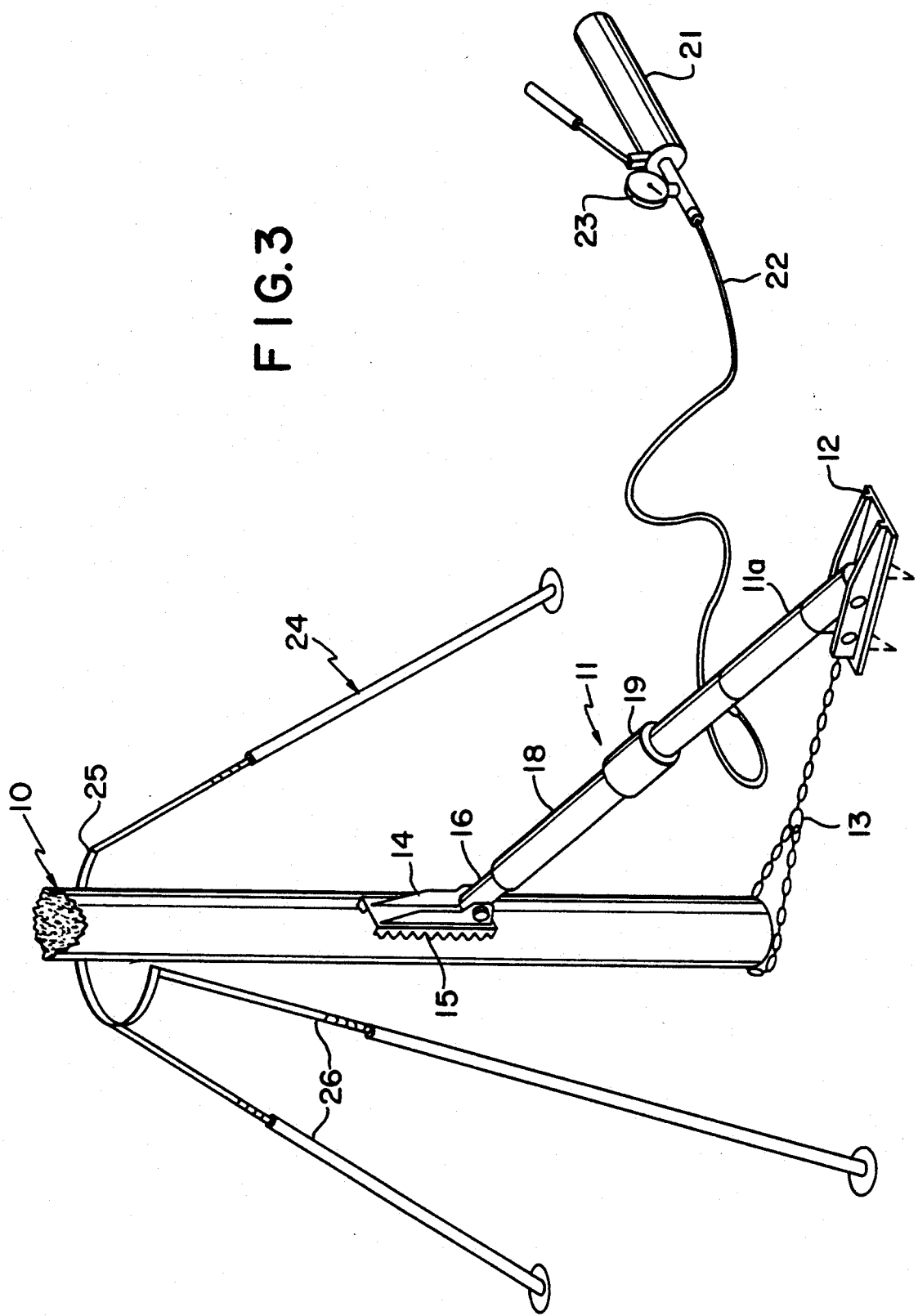
FIG. 3 is a perspective view of the apparatus for applying the load, or displacement, to the pole.

Referring to FIGS. 1 to 3, the residual strength of the pole 10 is measured by the displacement of the pole under a preset applied load of, eg. 100N.

Figure 4:
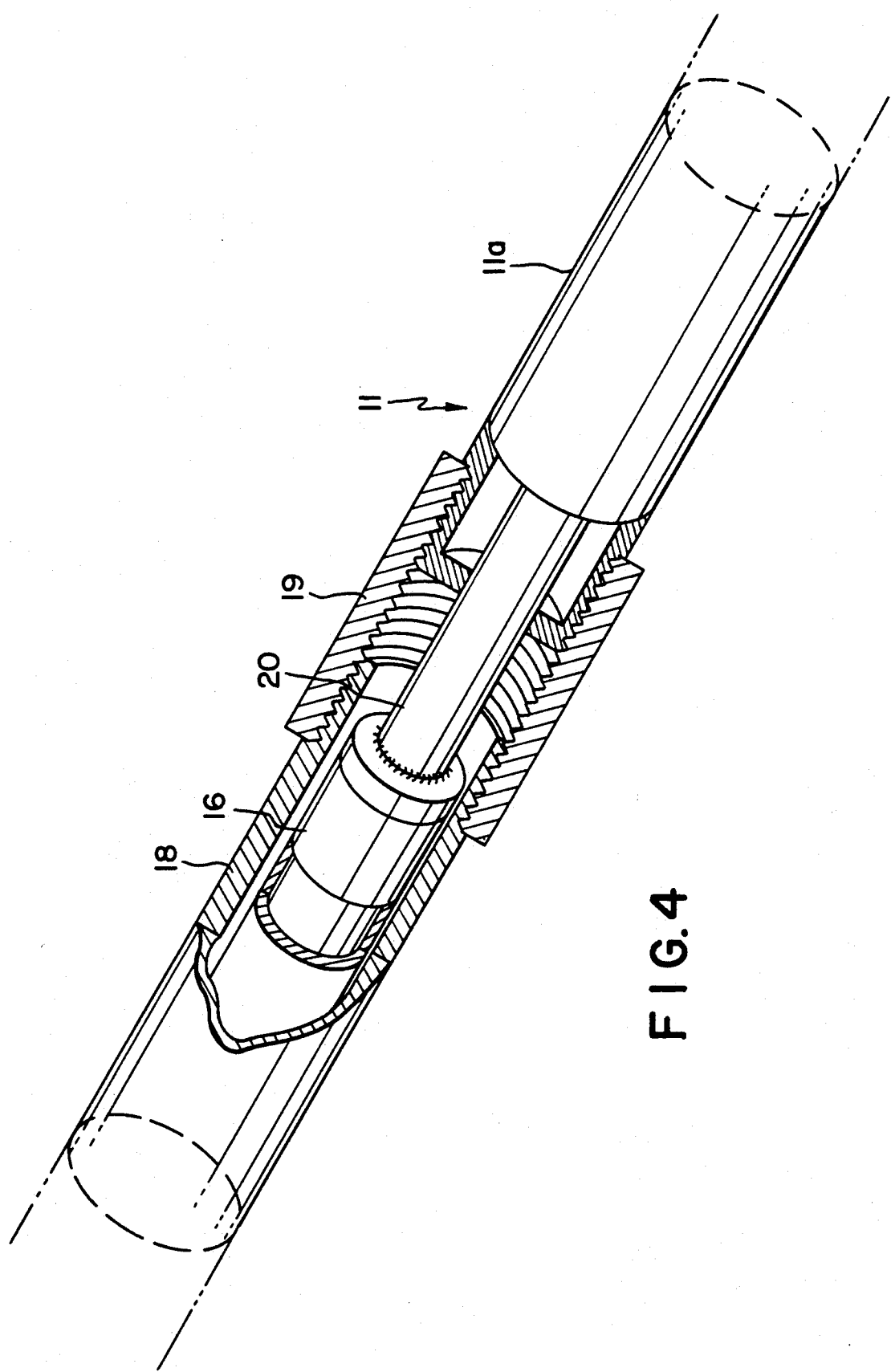
FIG. 4 is a part sectional view of a portion of the ram assembly of FIG. 3.

A pneumatic ram 11 is connected via a bottom tube 11a to a foot 12 anchored to the base of the pole by a chain 13. A head plate 14, with teeth 15, engages the pole 10 and may be releasably secured thereto by nails (not shown). The head plate 14 is mounted on an inner tube 16 telescopically received in an outer tube 17 secured to the ram body 18 by a sleeve 19, the inner end of the inner tube 16 being closed and engaged by the piston rod 20 of the ram 11 (see FIG. 4).

A hand operated pump 21 is connected to the ram 11 by a hose 22 and is fitted with an air pressure valve 23 to enable the applied load to be measured.

A safety frame 24 has a yoke 25 supported on three legs 26 and is positioned to catch and support the pole if the latter should fail under the applied load.

A reference frame 27 may be mounted on the safety frame, or be fixed in the ground, to provide a base reference for a plurality of spaced displacement gauges 28 which are releasably attached to the pole 10. In operation, the ram 11 is extended by operating the pump 21 until a preset load, indicated by the gauge 23, is applied to the pole 11.

The displacement of the pole is read off the displacement gauges 28 (i.e. the dial gauges) and the residual strength of the pole is calculated by feeding the applied load and displacement into a programmed hand calculator. (Information such as the height and diameter of the pole; the maximum expected wind forces; the type and number of conductors; and the spacing between the pole and its adjacent poles will have been programmed to display, e.g. the maximum applied load and the direction thereof to be applied to the pole.)

If the residual strength of the pole is calculated to be below a set threshold, the pole will be replaced.

Referring now to FIG. 2, the pole 10 is pushed by the ram 11 to a preset displacement, as measured by the displacement gauges 28, and the applied load is read off the gauge 23. The load applied to the pole to generate the present displacement enables the residual strength to be calculated using the calculator or from the tabulated figures.

As shown in FIG. 2, the output of the displacement gauges 28 can be fed directly into the calculator or computer 30 which has a central processor 31 (with a RAM) and a programmed memory 32. The variables such as applied load and pole diameter can be entered via the keyboard 33 and the residual strength may be displayed on a visual display 34 and/or via a printer 35. It will be readily apparent to the skilled addressee that all the data may be captured on site by a suitable recorder and processed later and the processed data may be stored in a history file.

In the method described with respect to FIG. 1, the test load will preferably be greater than the static load on the pole plus the maximum wind load due to any fittings plus an allowance for any additional decay before the next periodic test plus a safety factor. In the method described with reference to FIG. 2, the small test load which generates the preset displacement is extrapolated to calculate the maximum residual strength of the pole.

In a third method, the pole is tested under a Go/No Go situation. The minimum required strength for the pole is calculated based on the maximum wind velocity and any safety factors which must be allowed for. A load equivalent to the minimum required strength is applied to the pole using the ram 11 and the pole is observed. If the pole remains intact, it satisfies the minimum required strength and replacement is not required. This method can be used where the ultimate strength of the pole is not required.

Figure 5:
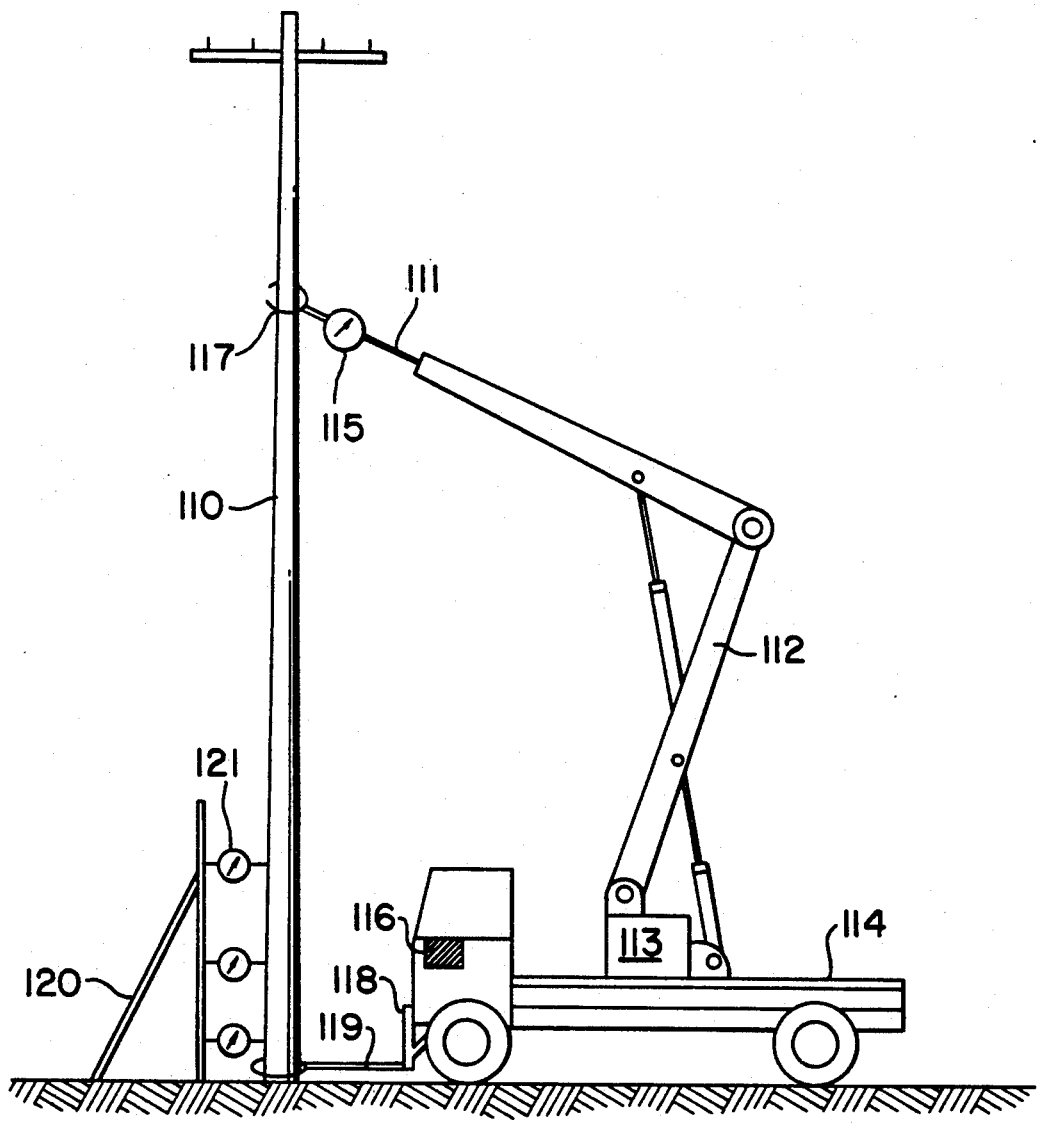
FIG. 5 is a schematic view showing a pole being tested under a preset load.

Referring now to FIG. 5, the residual strength of the pole 110 is measured by the displacement of the pole under a preset applied load of, e.g. 100 N.

A specially designed boom 111 is a part of a crane 112 powered by a hydraulic unit 113 mounted on a test vehicle 114. A load cell 115 electrically connected to the computer processing unit 116 measure the load applied to the pole 110 or otherwise the load is calculated directly from the pressure exerted in the hydraulic power unit 113. If necessary, the load is further resolved by a computer 116 into its horizontal and vertical components.

Safety clamps 117 are mounted at the end of the boom 111 to supported the pole both in horizontal and vertical direction should the pole fail under the applied load.

An adjustable length chain 119 is connected to a lowered frame 118 mounted to the test vehicle 114 to prevent the pole 110 from excessive horizontal movement at ground level.

A reference frame 120 provides a base from a plurality of spaced displacement gauges 121 mounted on the reference frame 120 or directly from the hydraulic power unit if the pole deflection is measured at the boom 11 level.

The residual strength of the pole 110 is calculated by feeding the applied load and displacement data into a programmed computer or preferably it can be computed and displayed automatically by the computer processing unit 116. The computer 116 also calculates the minimum required strength for the pole 110 based on the maximum loads applicable to the pole multiplied by a required safety factor allowing for any additional decay before the next periodic test. In this case, additional data are fed through the computer 116 including the size of pole 110, maximum wind forces, the direction, size, number and tension of the wires attached to the pole and other relevant factors. Preferably, the minimum required strength of the pole is determined in the office before the test.

Figure 6:
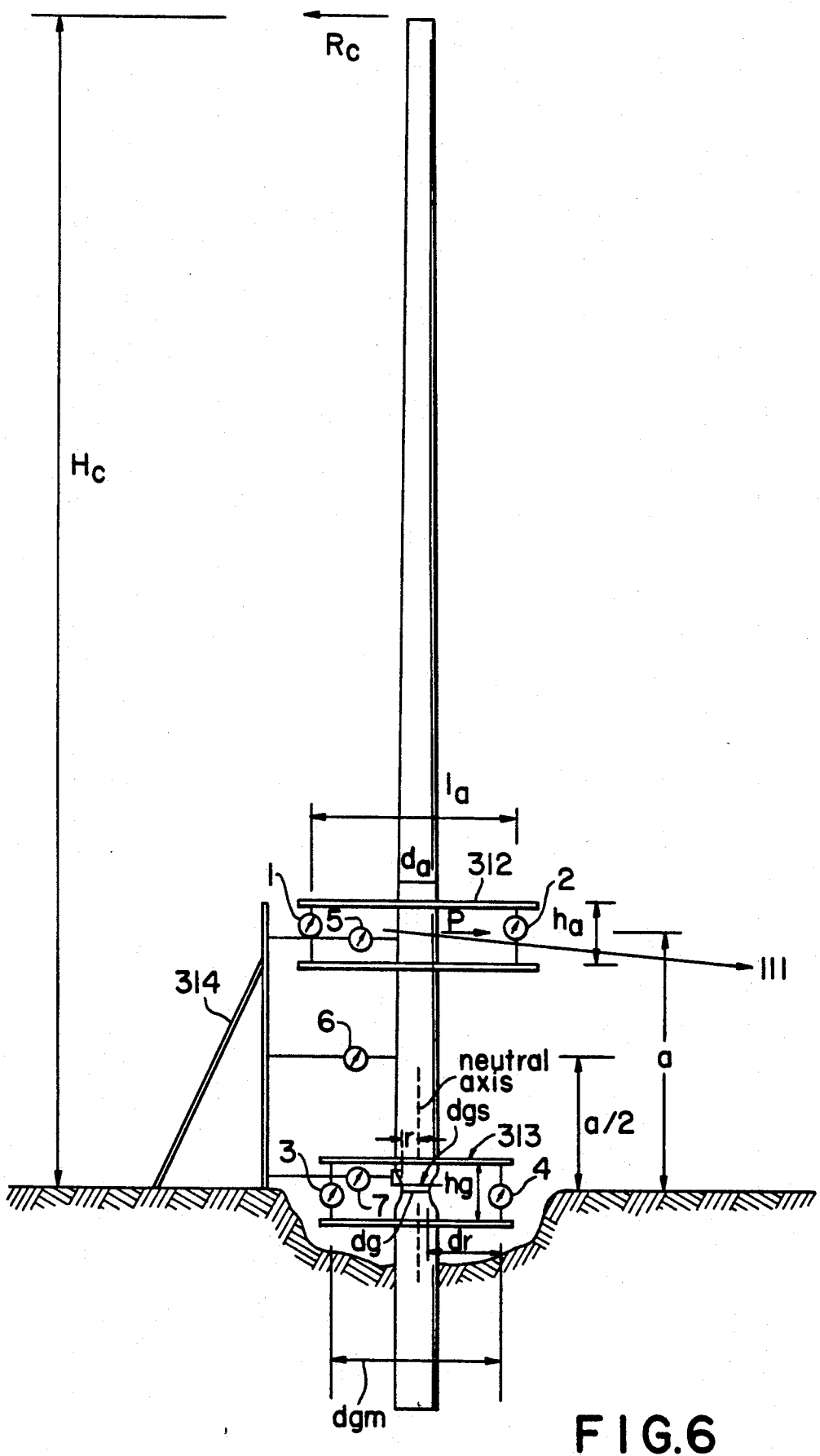
FIG. 6 is a diagram showing an arrangement of dial gauges to predict accurately the residual strength of substantially decayed poles.

Referring now to FIG. 6, the pole is pulled with a preset load P using the winch rope 111 and displacements of the pole are measured using the dial gauges 1 to 7 in order to determine the ultimate bending strength of the pole. The new method of the determination of the residual strength of decayed poles is explained in detail in Appendix 1.

Figure 7:
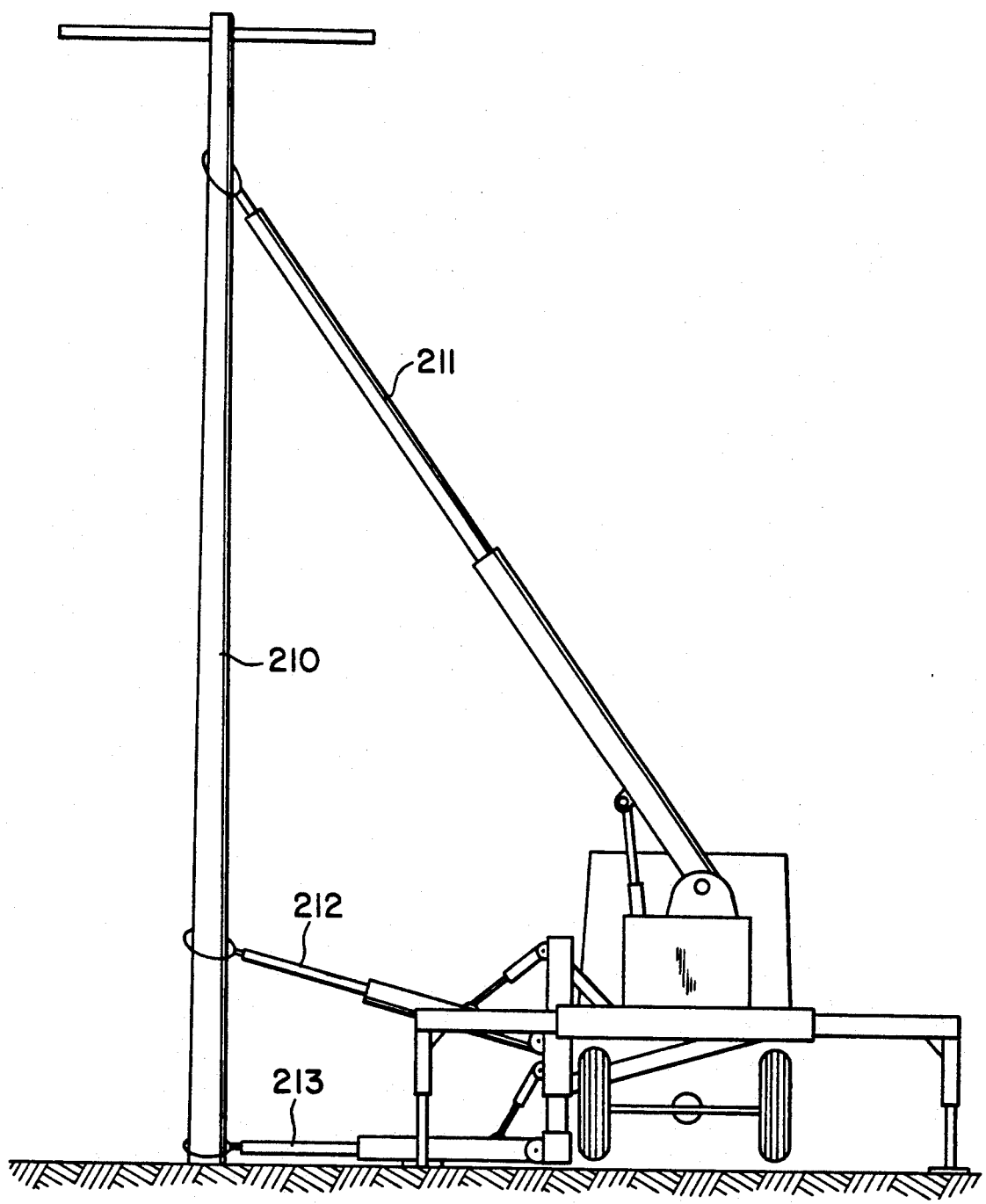
FIG. 7 is a schematic view showing the apparatus for proof loading of standing poles.

With reference to FIG. 7, the pole 210 is tested under a Go/No Go situation. The minimum required strength for the pole is calculated based on the maximum wind velocity and any safety factors which must be allowed for. A load (pushing or pulling) equivalent to the minimum required strength is applied to the pole using hydraulic rams 211, 212 and 213, and hand held or built in computer indicating the applicable oil pressure, and the pole and oil pressure is observed. If the pole fails (oil pressure drops), it must be reinforced or replaced. If the pole remains intact, it satisfies the minimum required strength and replacement is not required. This method can be used where the ultimate strength of the pole is not required.

Figure 8:
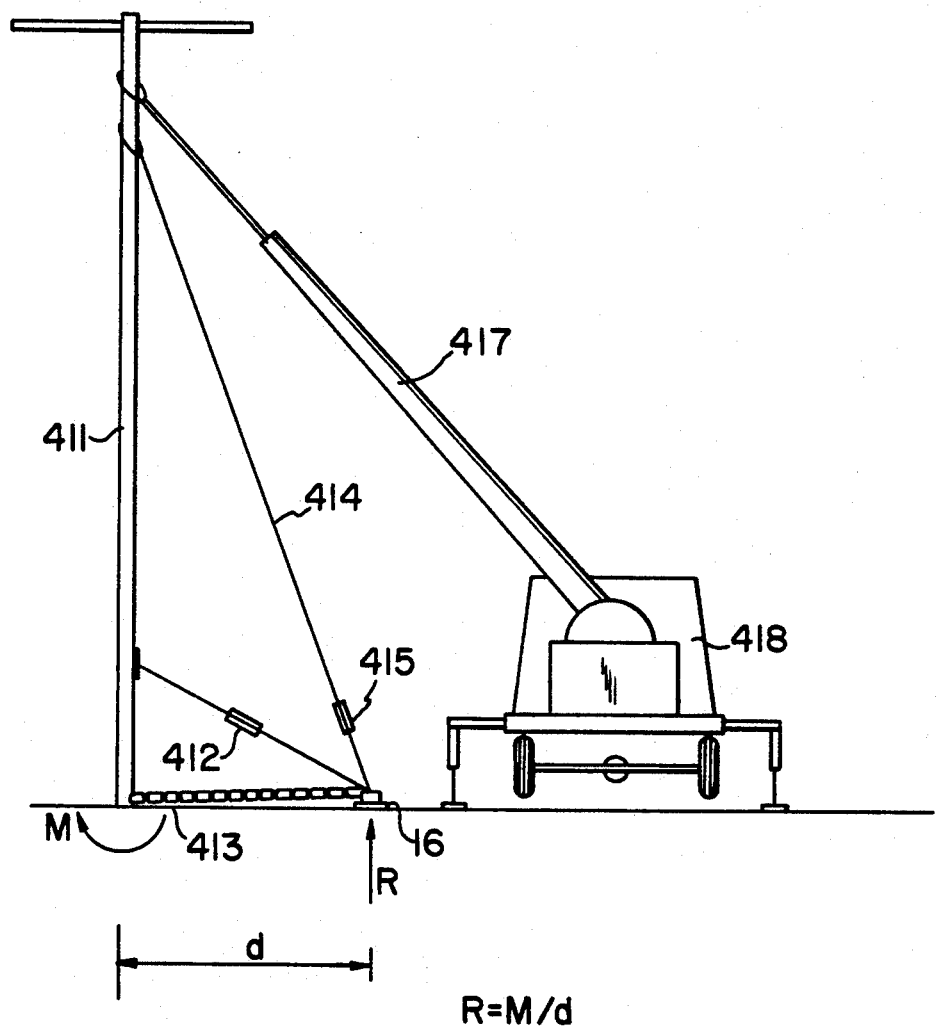
FIG. 8 is a schematic view showing a pole being tested with a portable hydraulic ram.

Referring to FIG. 8, a pole 411 is pushed with a hydraulic ram 412 and simultaneously pulled with a chain 413 and tension rope 414, tensioned by winch 415 until a preset load R is obtained on a load cell 416.

Having the values of the predetermined required strength of pole M and constant distance d between the load cell 416 and pole 411, the load R can be easily calculated from the following formula:

$$R = M/d$$

Stability of the pole in case of its failure is provided by a safety boom 417 of a truck 418. During the test there is no contact between the safety boom 417 and pole 411.

Figure 9:
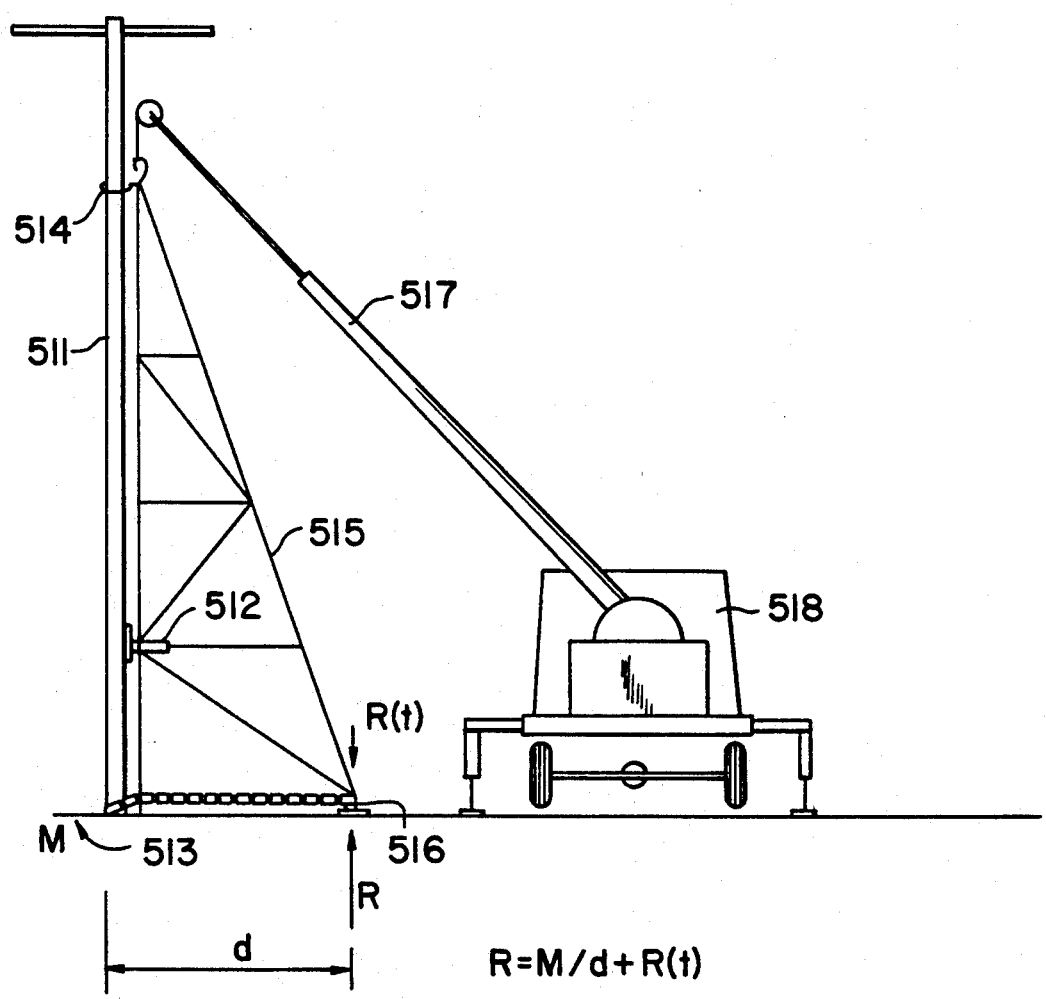
FIG. 9 is a schematic view showing a pole being tested with a specially designed steel truss operated with a crane mounted on a truck.

Referring now to FIG. 9, a pole 511 is pushed with a hydraulic ram 512 mounted on a truss 515 and simultaneously pulled with a chain 513 and a hook 514 attached to the truss 515 until a preset load R is obtained on a load cell 516.

A truss 515 is operated by a crane boom 517 mounted on a truck 518. During the test the truss is resting on the ground, the pole 511 and the load cell 516 and is only loosely hooked to the boom so that there are no forces transmitted between the truss and the boom of the truck.

Having the values of the pre-determined required strength of pole M and constant distance d between the load cell 516 and pole 511, the load R can be easily calculated from the following formula:

$$R = M/d + R(t)$$

where:
R(t)—reaction from the weight of the truss acting on the load cell 16. It can be read from the load cell before the hydraulic ram 12 is activated.

Stability of the pole in case of its failure is provided indirectly (through the truss) by the safety boom 17 of the truck.

Figure 10:
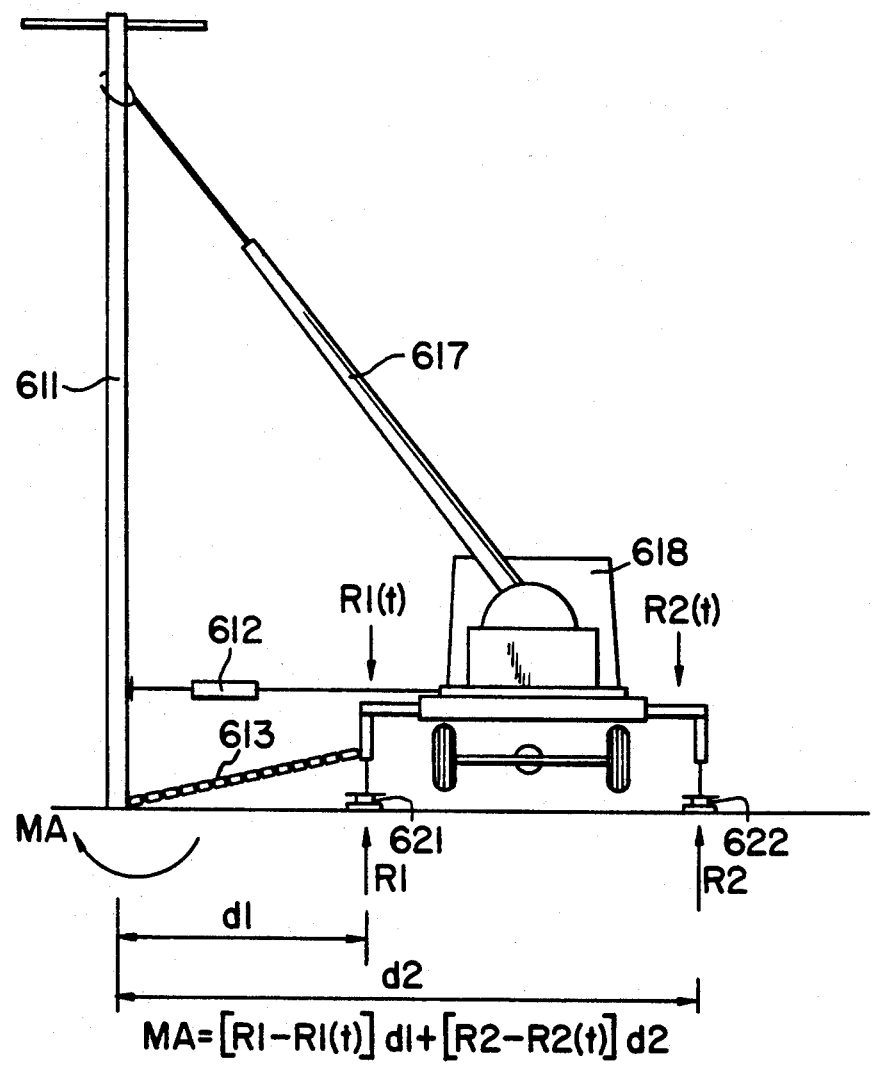
FIG. 10 is a schematic view showing a pole being tested with a hydraulic ram and crane mounted on a truck.

With reference to FIG. 10, a pole 611 is pushed or pulled with a hydraulic ram 612 mounted on a truck 618 and simultaneously pulled or pushed with a passive arm 613 and active boom 617 mounted on the truck until a pre-determined bending moment M on the pole 611 is obtained. During the test the outriggers of the truck 618 rest on load cells 621 and 622.

Having the values of distances d1 and d2 as well as load readings R1 and R2 on load cells 621 and 622 respectively, the actual bending moment MA applied to the pole can be checked easily using the following formula:

$$MA = [R1 - R1(t)]d1 + [R2 - R2(t)]d2$$

where:
MA—actual bending moment applied to the pole at ground level.
R1—load read from load cell 621.
R2—load read from load cell 622.
R1(t)—reaction from the weight of the truck acting on the load cell 621. It can be read from the load cell before the hydraulic ram 612 is activated.
R2(t)—reaction from the weight of the truck acting on the load cell 622. It can be read from the load cell before the hydraulic ram 612 is activated.
d1—distance between the pole 611 and load cell 621.
d2—distance between the pole 611 and load cell 622.

The load generated by the hydraulic ram 612 may need to be increased several times before the actual bending moment MA is equal or greater than the minimum required bending strength of pole M.

Stability of the pole in case of its failure is provided by the load and safety boom 617 of the truck.

Figure 11:
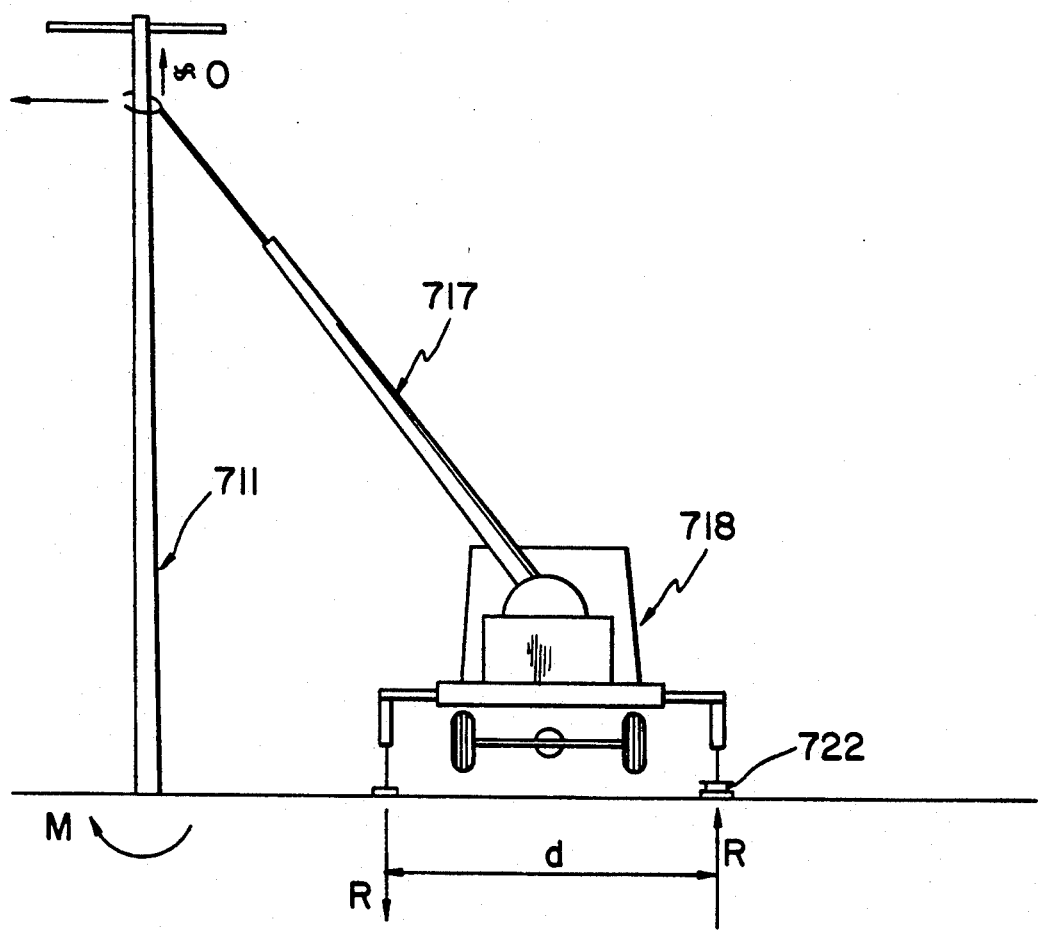
FIG. 11 is a schematic view showing a pole being tested with a hydraulic crane mounted on a truck.
Figure 12:
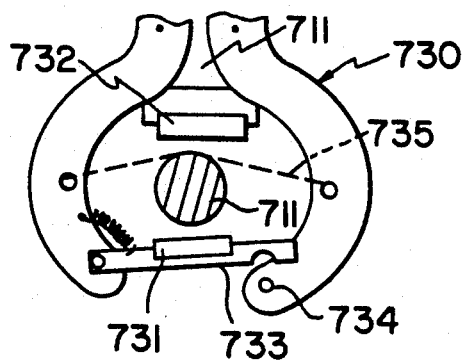
FIG. 12 is a schematic plan view of the jaws on the crane of FIG. 11.
Figure 13:
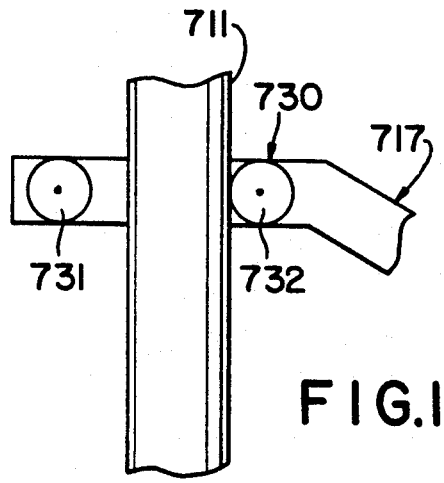
FIG. 13 is a schematic side view showing the roller and pole of FIG. 12.

Referring now to FIG. 11, the pole 711 is pushed or pulled with a hydraulic crane jib 717, with jaws 730 (see FIGS. 12, 13) until a predetermined bending moment M on the pole 711 is obtained. During the test, one of the outriggers of the truck 718 rests on a load cell 722.

The jaws 730 (see FIGS. 12 and 13) are provided so that the vertical component of the force applied to the pole 711 is equal (or substantially equal) to zero and so only a horizontal component is applied to the pole.

The bending moment applied to the pole is calculated by the formula:

$$R = k \times M/d$$

where:
R = load transferred to ground after deduction of truck weight.
k = ratio of total load transferred to ground via rear legs.
M = bending moment applied to pole base.
d = distance between rear legs.
d is a constant, and k is a constant ($0.9 \leq k \leq 0.95$). (The front of the truck is not supported by outriggers and the twisting of the truck chassis will reduce the percentage of load transferred via the front wheels and their suspension.)

As the value of M is preset, the jib is extended until the desired value of R is achieved.

The angle and length of the jib 717 and the distance of the truck 718 from the pole 711 have no effect. The jib 717 must be square to the truck or the value of k will change.

The jaws 730 on the distal end of the jib 711 have a pair of rollers 731, 732 which can bear against the pole 711. The inner roller 732 has an axle journalled on plates on the end of the jib 717, while the outer roller 731 is mounted on an axle journalled on a hinged, spring-loaded locking bar 733, which can engage a pin to prevent the pole 711 escaping from the jaws 730 should the pole fail under test.

In certain applications, eg. where the rollers cannot be brought to bear on the pole, a chain 735 can span the jaws to engage the pole 711.

Figure 14:
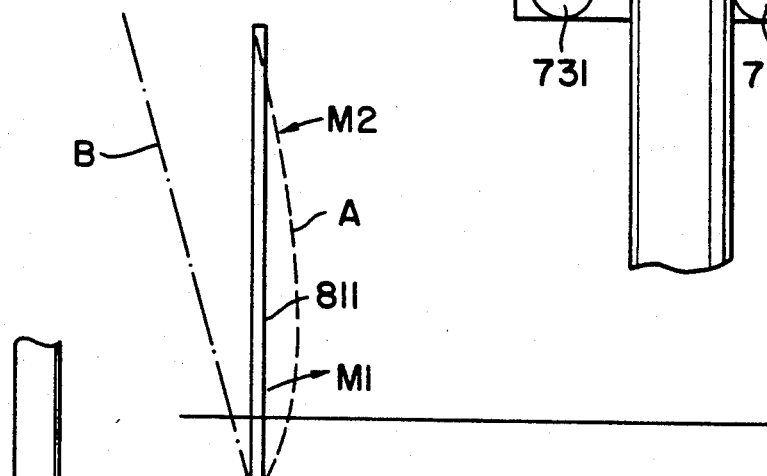
FIG. 14 is a schematic view showing the preferred deflection of a pole in soft soil and/or where services extend to both sides of the pole.

In soft soil, or where the service lie parallel to the applied bending moment (see FIG. 14), a load M1 is applied towards the truck at the base of the pole 811 and the applied bending moment is applied in the direction of arrow M2 (see line A) so that the services will not be excessively displaced as would occur if load M1 were not applied —see line B.

Figure 15:
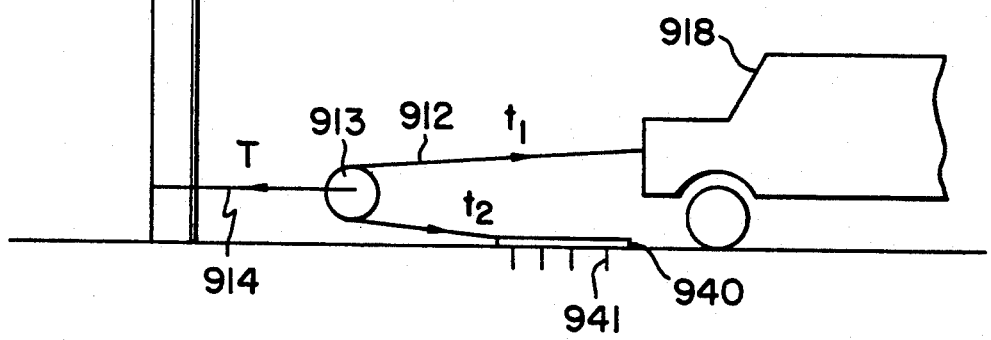
FIG. 15 is a schematic view of a cable (or chain) and pulley connection between a pole and a vehicle.

Referring to FIG. 15, the load applied to the base of the pole 911 can be doubled by anchoring one end of a cable or chain 912 to a base plate 940, anchored with pins or spikes 941, and the other end to the truck 918, the cable 912 passing around a pulley 913 secured by a cable 914. Load T applied to the pole equals the loads $t_1$ and $t_2$ on the cable 912.

In all the embodiments illustrated in FIGS. 8, 9, 10 and 11, the pole is tested under a Go/No Go situation. During the loading both the pole and load cell readings are closely observed. If the pole fails, ie. the pole cracks and load cell reading drops suddenly, the pole is considered unsafe and sooner or later it must be either reinforced or replaced.

The great value of the presented method resides in the fact that despite a complex structural model of the test, including several unknown interactive forces and loads as well as unknown foundation and pole characteristics, only one or few readings are required to check whether a pole has a required strength.

It will be readily apparent to the skilled addressee that the present invention provides simple, efficient and reliable means for determining the residual strength of poles in a non-destructive manner (unless the pole's strength is below a preset safety level).

Various changes and modifications may be made to the embodiments described without departing from the scope of the present invention defined in the appended claims.

I claim:

1. A method for testing the residual strength of a pole, including the steps of:
   calculating a minimum allowable residual strength for the pole (at which the pole requires replacement) from a predetermined formula (e) or by a programmed calculator or computer;
   applying a preset load, corresponding to the minimum allowable residual strength, to the pole by pushing or pulling the pole above ground level;
   restraining the pole substantially at ground level using at least one of a chain, a cable and a ram; and
   observing if the pole fails under the applied load if the actual residual strength of the pole is below the minimum allowable residual strength.

2. A method according to claim 1 wherein:
   the minimum allowable residual strength of the pole is dependent on factors including the height and diameter of the pole, type and number of conductors supplied by the pole, the spacing between the pole and adjacent poles, and the estimated maximum wind forces on the pole.

3. A method according to claim 1 further including observing a displacement of the pole such that the pole is observed to fail if it exceeds a preset displacement from its vertical axis under the applied load.

4. Apparatus for testing the residual strength of a pole, comprising:
   calculator or computer means for calculating a minimum allowable residual strength M for the pole (at which the pole requires replacement) and thereby a corresponding load to be applied to the pole;
   means for applying the load to the pole by pushing or pulling the pole above ground level;
   means for measuring load applied to the pole comprising a load cell or gauge; and
   means for observing if the pole fails under the applied load if the actual residual strength is below the minimum allowed residual strength.

5. An apparatus as claimed in claim 4 wherein:
   the load is applied by a pneumatic or hydraulic ram which has a cylinder with a foot anchored thereto, the foot being spaced from the pole and anchored by 1) a cable or chain connected to the pole at ground level and 2) engaging spikes; and
   a head plate engaged with the pole, the head plate being fixed to the distal end of an inner tube which is telescopically received in an outer tube mounted on the ram, the inner tube being engaged by the piston rod of the ram.

6. An apparatus according to claim 4, further comprising a vehicle;
   wherein a pneumatic or hydraulic ram is incorporated in a boom which is mounted on the vehicle, the boom has a distal end which engages the pole, and the means for applying the load to the pole includes the pneumatic or hydraulic ram.

7. An apparatus according to claim 6 wherein the means for measuring load comprises at least one of strain gauges and displacement gauges mounted on a support frame and connected to the pole.

8. An apparatus according to claim 4 wherein the means for applying the load to the pole includes a hydraulic ram and and at least one of a chain and a tension rope tensioned by a winch, the pole being simultaneously pushed by the hydraulic ram and pulled by the at least one of the chain and the tension rope until a preset load R is obtained on a load cell at a distance d from the pole, the preset load R being calculated by the formula $R = M/d$.

9. An apparatus according to claim 8, wherein a safety boom is mounted on a vehicle to engage and support the pole if it fails under the applied load.

10. An apparatus according to claim 4 wherein in soft soil, or when the applied load is parallel to the services supported by the pole, the applied load has a first bending moment in one direction at ground level and a second bending moment in the opposite directions intermediate the pole so that the displacement of the top of the pole is minimised.

11. Apparatus according to claim 4, wherein the load applied to the pole at ground level is applied by a first cable or chain attached to a pulley; and
    a second cable or chain is anchored at one end to the ground and passes around the pulley and is connected at its other end to a vehicle.

12. Apparatus for testing the residual strength of a pole, comprising:
    calculator or computer means for calculating a minimum allowable residual strength M for the pole (at which the pole requires replacement) and thereby a corresponding load to be applied to the pole;
    means for applying the load to the pole by pushing or pulling the pole above ground level;
    means for measuring load applied to the pole comprising a load cell or gauge;

means for observing if the pole fails under the applied load if the actual residual strength is below the minimum allowed residual strength; and a vehicle;

wherein a pneumatic or hydraulic ram is incorporated in a boom which is mounted on the vehicle, the boom has a distal end which engages the pole, and the means for applying the load to the pole includes the pneumatic or hydraulic ram; and wherein the load cell is provided on the boom and a computer on the vehicle resolves the load applied to the pole, measured by the load cell, into its horizontal and vertical components.

13. Apparatus for testing the residual strength of a pole, comprising:

calculator or computer means for calculating a minimum allowable residual strength M for the pole (at which the pole requires replacement) and thereby a corresponding load to be applied to the pole;

means for applying the load to the pole by pushing or pulling the pole above ground level;

means for measuring load applied to the pole comprising a load cell or gauge;

means for observing if the pole fails under the applied load if the actual residual strength is below the minimum allowed residual strength; and a vehicle;

wherein a pneumatic or hydraulic ram is incorporated in a boom which is mounted on the vehicle, the boom has a distal end which engages the pole, and the means for applying the load to the pole includes the pneumatic or hydraulic ram; and wherein a chain or cable is connected to the vehicle to prevent excessive horizontal movement of the pole at ground level.

14. Apparatus for testing the residual strength of a pole, comprising:

calculator or computer means for calculating a minimum allowable residual strength M for the pole (at which the pole requires replacement) and thereby a corresponding load to be applied to the pole;

means for applying the load to the pole by pushing or pulling the pole above ground level;

means for measuring load applied to the pole comprising a load cell or gauge;

means for observing if the pole fails under the applied load if the actual residual strength is below the minimum allowed residual strength; and a vehicle;

wherein a pneumatic or hydraulic ram is incorporated in a boom which is mounted on the vehicle, the boom has a distal end which engages the pole, and the means for applying the load to the pole includes the pneumatic or hydraulic ram; and wherein safety clamps are provided at the distal end of the boom to support the pole in both the horizontal and vertical directions should the pole fail under the applied load.

15. Apparatus for testing the residual strength of a pole, comprising:

calculator or computer means for calculating a minimum allowable residual strength M for the pole (at which the pole requires replacement) and thereby a corresponding load to be applied to the pole;

means for applying the load to the pole by pushing or pulling the pole above ground level;

means for measuring load applied to the pole comprising a load cell or gauge;

means for observing if the pole fails under the applied load if the actual residual strength is below the minimum allowed residual strength; and a vehicle;

wherein a pneumatic or hydraulic ram is incorporated in a boom which is mounted on the vehicle, the boom has a distal end which engages the pole, and the means for applying the load to the pole includes the pneumatic or hydraulic ram; and wherein the load is further applied to the pole by a second hydraulic ram at ground level and a third hydraulic ram intermediate the distal end of the boom and the second hydraulic ram;

the vehicle is supported on outriggers; and the oil pressure in the respective hydraulic rams is measured, where a fall in oil pressure under the applied load indicates failure of the pole.

16. Apparatus for testing the residual strength of a pole, comprising:

calculator or computer means for calculating a minimum allowable residual strength M for the pole (at which the pole requires replacement) and thereby a corresponding load to be applied to the pole;

means for applying the load to the pole by pushing or pulling the pole above ground level;

means for measuring load applied to the pole comprising a load cell or gauge;

means for observing if the pole fails under the applied load if the actual residual strength is below the minimum allowed residual strength;

wherein the means for applying load to the pole includes a truss, a hydraulic ram mounted on the truss, a chain connected to the truss and a first location on the pole, and a hook connected to the truss and a second location on the pole, and wherein the hydraulic ram applies a load to the pole between the first and second locations; and a preset load R is measured on a load cell engaged by the truss.

17. An apparatus according to claim 16 wherein the truss rests on the ground during the test and is supported from a boom on a vehicle for transport.

18. Apparatus for testing the residual strength of a pole, comprising:

calculator or computer means for calculating a minimum allowable residual strength M for the pole (at which the pole requires replacement) and thereby a corresponding load to be applied to the pole;

means for applying the load to the pole by pushing or pulling the pole above ground level;

means for measuring load applied to the pole comprising a load cell or gauge;

means for observing if the pole fails under the applied load if the actual residual strength is below the minimum allowed residual strength; and a vehicle;

wherein a pneumatic or hydraulic ram is incorporated in a boom which is mounted on the vehicle, the boom has a distal end which engages the pole, and the means for applying the load to the pole includes the pneumatic or hydraulic ram; and wherein the vehicle is supported on outriggers having respective load cells, the bending moment applied to the pole being calculated from the loads measured on the load cells and their respective distances from the pole such that the applied bending moment is set equal to or greater than a minimum required pole bending strength.

19. An apparatus according to claim 18, wherein the pole is pushed by a second hydraulic ram mounted on the vehicle and pulled by a chain on the vehicle.

20. Apparatus for testing the residual strength of a pole, comprising:
- calculator or computer means for calculating a minimum allowable residual strength M for the pole (at which the pole requires replacement) and thereby a corresponding load to be applied to the pole;
- means for applying the load to the pole by pushing or pulling the pole above ground level;
- means for measuring load applied to the pole comprising a load cell or gauge;
- means for observing if the pole fails under the applied load if the actual residual strength is below the minimum allowed residual strength; and
- a vehicle;
- wherein a pneumatic or hydraulic ram is incorporated in a boom which is mounted on the vehicle, the boom has a distal end which engages the pole, and the means for applying the load to the pole includes the pneumatic or hydraulic ram; and
- wherein the boom is provided with jaws at its distal end to engage the pole with a substantially zero vertical applied load;
- the vehicle is supported by a pair of outriggers;
- a bending moment is applied to the pole due to the applied load, the bending moment being calculated by the formula $R = k \times M/d$ where the R is the measured applied load, d is the distance between the outriggers and k is a constant for the vehicle such that the applied bending moment is set equal to or greater than a minimum required pole bending strength; and
- wherein the load cell is provided on one of the outriggers.

21. An apparatus according to claim 20, wherein $0.9 \leq k \leq 0.95$.

22. Apparatus according to claim 20, wherein the jaws have a pair of spaced, parallel rollers to engage opposite sides of the pole, one of the rollers being mounted on a hingedly mounted locking bar to releasably secure the pole in the jaws, should the pole fail under the applied load.

23. Apparatus according to claim 22 wherein a chain extends across the jaws to engage the pole when the rollers cannot be aligned with the pole.

* * * * *